United States Patent
Charles

(10) Patent No.: US 10,555,834 B2
(45) Date of Patent: Feb. 11, 2020

(54) VITRECTOMY PROBE WITH ROTARY CUTTER AND ASSOCIATED DEVICES, SYSTEMS, AND METHODS

(71) Applicant: Novartis AG, Basel (CH)

(72) Inventor: Steven T. Charles, Memphis, TN (US)

(73) Assignee: Novartis AG, Basel (CH)

( * ) Notice: Subject to any disclaimer, the term of this patent is extended or adjusted under 35 U.S.C. 154(b) by 492 days.

(21) Appl. No.: 15/239,601

(22) Filed: Aug. 17, 2016

(65) Prior Publication Data

US 2018/0008463 A1  Jan. 11, 2018

Related U.S. Application Data

(60) Provisional application No. 62/360,752, filed on Jul. 11, 2016.

(51) Int. Cl.
*A61F 9/007* (2006.01)
*A61B 17/00* (2006.01)

(52) U.S. Cl.
CPC  *A61F 9/00763* (2013.01); *A61B 2017/00544* (2013.01)

(58) Field of Classification Search
CPC ......... A61B 2017/00544; A61B 2017/320098; A61B 2017/320028; A61B 2017/320032; A61B 10/0233; A61B 10/0275; A61B 10/0283; A61B 17/320783; A61B 17/320016; A61B 17/32002; Y10T 74/18008; Y10T 74/18016; A61F 9/00763
USPC ...................................................... 74/20, 45
See application file for complete search history.

(56) References Cited

U.S. PATENT DOCUMENTS

| | | | |
|---|---|---|---|
| 2006/0116605 A1* | 6/2006 | Nakao | A61B 10/0266 600/566 |
| 2010/0125287 A1* | 5/2010 | Cole | A61B 17/32053 606/133 |
| 2011/0196400 A1* | 8/2011 | Robertson | A61B 17/22004 606/169 |
| 2012/0245569 A1 | 9/2012 | Papac | |
| 2014/0171996 A1 | 6/2014 | McDonell | |
| 2015/0282928 A1 | 10/2015 | Auld et al. | |
| 2016/0015511 A1 | 1/2016 | Auld et al. | |

(Continued)

FOREIGN PATENT DOCUMENTS

| | | |
|---|---|---|
| EP | 0514057 A1 | 11/1992 |
| WO | 2008079526 A2 | 7/2008 |

*Primary Examiner* — Erich G Herbermann

(57) ABSTRACT

Systems, apparatuses, and methods of and for an ophthalmic surgical system are disclosed. An ophthalmic surgical system may include a vitrectomy probe having a housing sized and shaped for grasping by a user. The vitrectomy probe may also include a cutter extending from the housing and being sized to penetrate and treat a patient eye. The cutter may include an outer cutting tube coupled to the housing. The outer cutting tube may have an outer port formed therein that is sized and shaped to receive tissue. The cutter may include a rotatable inner cutting member disposed within the outer cutting tube. The inner cutting member may include a first cutting surface that rotates across the outer port to cut the tissue when the inner cutting member is rotated. The vitrectomy probe may include a pneumatic vane actuator positioned within the housing and configured to rotate the inner cutting member.

2 Claims, 12 Drawing Sheets

(56) References Cited

U.S. PATENT DOCUMENTS

2016/0067036 A1 3/2016 Auld
2017/0333252 A1 11/2017 Biancalana et al.

* cited by examiner

VITRECTOMY PROBE WITH ROTARY CUTTER AND ASSOCIATED DEVICES, SYSTEMS, AND METHODS

CROSS-REFERENCE TO RELATED APPLICATIONS

This application claims the benefit of U.S. Provisional Application No. 62/360,752, filed Jul. 11, 2016, the entire contents of which are incorporated herein by reference.

TECHNICAL FIELD

The present disclosure is directed to ophthalmic surgical devices, systems, and methods. More particularly, but not by way of limitation, the present disclosure is directed to vitrectomy probe with a rotary cutter.

BACKGROUND

Microsurgical procedures frequently require precision cutting and/or removing of various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g., cutting and removal of vitreous near a detached portion of the retina or a retinal tear), vitreous base dissection, and cutting and removal of membranes are particularly difficult.

Conventional vitrectomy probes can be divided into two types: axial or "guillotine style" probes and rotational probes. An axial or guillotine style probe has an inner cutting member that reciprocates in a translational manner along its longitudinal axis. The inner cutting member is positioned within an outer cutting member that includes a port at its distal end. Vitreous humor and/or membranes are aspirated into the open port of the outer cutting member. The vitreous and/or membranes are cut as the inner cutting member reciprocates. The cut tissue is then aspirated away from the eye. The inner cutting member may reciprocate at a rate between several tens to several hundred times per second. The reciprocal movement of the inner cutting member may produce an undesirable pumping action or pulsatile flow that pushes fluid out of the port as the inner cutting member moves towards the port and draws additional fluid into the port as the inner cutting member moves away from the port.

A rotational or rotary probe has an inner cutting member that rotates at a high rate around its longitudinal axis. Continuous rotation of the inner cutting member may cause undesired winding and/or tearing (as opposed to cutting) of the vitreous collagen fibers. Some rotational probes have attempted to address this issue by replacing continuous rotation of the inner cutting member with limited rotary action drive mechanisms that limit angular rotation. Limited rotary action drive mechanisms, however, could not be implemented in small gauge vitrectomy probes because of spiral torsional failure during reciprocation of the inner cutting member.

SUMMARY

The present disclosure describes example ophthalmic surgical systems that may include a vitrectomy probe. The vitrectomy probe may include a housing sized and shaped for grasping by a user. The vitrectomy probe may also include a cutter extending from the housing and being sized to penetrate and treat an eye of a patient. The cutter may include an outer cutting tube coupled to the housing. The outer cutting tube may have an outer port formed therein. The outer port may be sized and shaped to receive tissue. The cutter may include an inner cutting member disposed within the outer cutting tube. The inner cutting member may be rotatable about a longitudinal axis thereof. The inner cutting member may include a first cutting surface that rotates across the outer port to cut the tissue when the inner cutting member is rotated. The vitrectomy probe may include a pneumatic vane actuator positioned within the housing and coupled to the inner cutting member. The pneumatic vane actuator may be configured to rotate the inner cutting member.

In addition, the present disclosure is directed to ophthalmic surgical methods. An exemplary method may include inserting a cutter of a vitrectomy probe into a vitreous chamber of an eye of a patient. The cutter may include an outer cutting tube having an outer port sized and shaped to receive tissue. The cutter may include a rotatable inner cutting member positioned within the outer cutting tube and rotatable past the outer port. The method may include rotating the inner cutting member to cut tissue in the outer port by applying air pressure pulses to a pneumatic vane actuator disposed in the vitrectomy probe.

The present disclosure may also disclose ophthalmic surgical systems that include a vitrectomy probe. The vitrectomy probe may include a housing sized and shaped for grasping by a user. The vitrectomy probe may include a cutter sized to penetrate an eye and extend from the housing. The cutter may include an outer cutting tube coupled to the housing. The outer cutting tube may have an outer port formed therein. The outer port may be sized and shaped to receive tissue. The cutter may include an inner cutting member disposed within the outer cutting tube. The inner cutting member may be rotatable past the outer port. The inner cutting member may include a first cutting surface that rotates past the outer port to cut the tissue. The vitrectomy probe may include a drive shaft disposed within the housing. The vitrectomy probe may include an actuator coupled to the drive shaft and disposed within the housing. The actuator may be configured to impart translational motion to the drive shaft such that the drive shaft is linearly reciprocable in response to actuation by the actuator. The vitrectomy probe may include a drive member coupled to the drive shaft and the inner cutting member. The drive member may be configured to impart rotational motion to the inner cutting member such that the inner cutting member is rotatable in response to the linear reciprocable motion of the drive shaft.

In different implementations, the various aspects of the disclosure may include one or more of the following features. The pneumatic vane actuator may include a single vane actuator. The pneumatic vane actuator may include a dual vane actuator. The inner cutting member may include a tube. The inner cutting member may include an aspiration lumen arranged to aspirate tissue from the eye. The inner cutting member may include a rod. The outer cutting tube may include a lumen sized to pass tissue adjacent the rod for aspiration from the eye. The pneumatic vane actuator may be configured to reciprocate the inner cutting member such that the inner cutting member rotates in a first direction and in a second direction opposite the first direction. A first air pressure pulse may be applied to a first chamber of the pneumatic vane actuator to rotate the inner cutting member in the first direction, and a second air pressure pulse may be applied to a second chamber of the pneumatic vane actuator to rotate the inner cutting member in the first direction. A first vacuum pulse may be applied to the second chamber simultaneously with the first air pressure pulse being applied to the first chamber, and a second vacuum pulse may be applied to the first chamber simultaneously with the second air pressure pulse being applied to the second chamber. The first and second air pressure pulses are applied 180° out of phase from one another. The inner cutting member may further include a second cutting surface. The first cutting surface may be positioned within the outer cutting tube adjacent to the outer port to cut the tissue when the inner cutting member is rotated in the first direction. The second cutting surface may be positioned within the outer cutting member adjacent to the outer port to cut the tissue when the inner cutting member is rotated in the second direction. The inner cutting member may be configured to reciprocate in the first and second directions along an arc. The arc may span less than 90°.

Rotating the inner cutting member may include rotating the inner cutting member in alternating first and second directions by applying alternating air pressure pulses to first and second chambers of the pneumatic vane actuator.

The drive member configured to impart rotational motion to the inner cutting member may include a swash plate. The drive member may include a screw drive. The drive member may be disposed in the outer cutting tube.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

Figure 1:
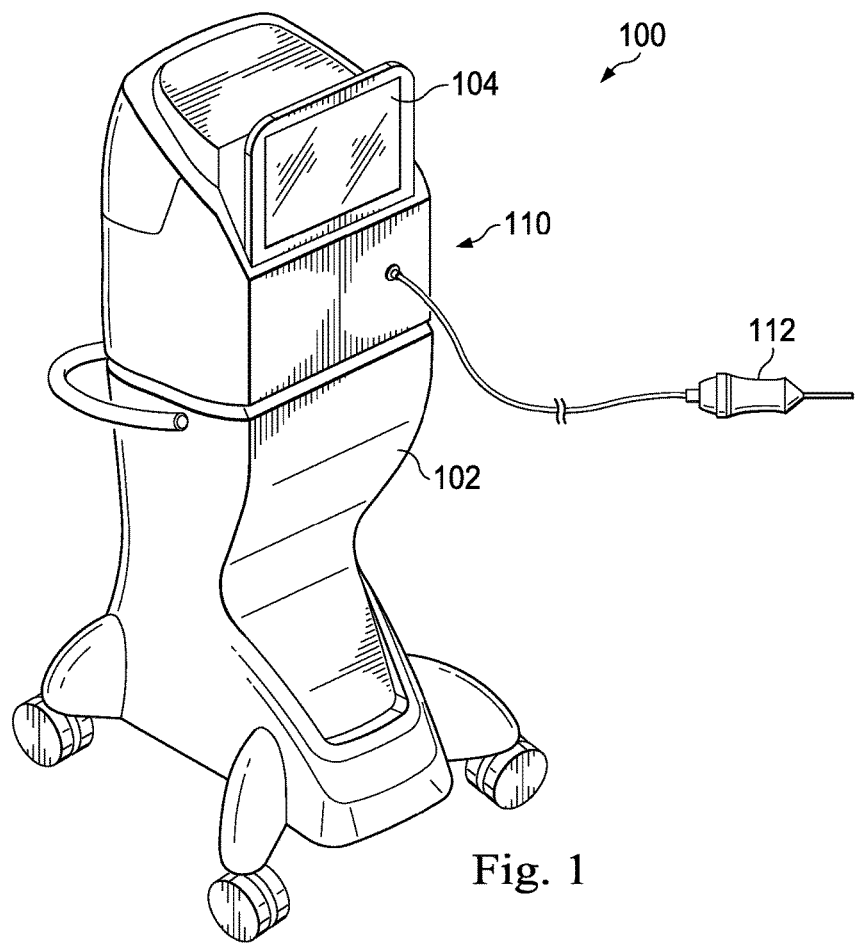
FIG. 1 is an illustration of an example ophthalmic surgical system.

These figures will be better understood by reference to the following Detailed Description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure relates generally to devices, systems, and methods for cutting tissue within the eye using a limited rotary action vitrectomy cutter. In some implementations, the rotary action may be achieved using pneumatic drive mechanisms. For example, some implementations may utilize a pneumatic vane actuator to drive a rotatable inner cutting member along an arc in opposite first and second directions. Alternating pressure pulses and/or vacuum pulses may drive the vane actuator. The inner cutting member may include two cutting surfaces at opposing ends such that tissue may be cut while the inner cutting member rotates in a first direction and while the inner cutting member moves in an opposing second direction. In some implementations, the angular profile of the arc through which the inner cutting member rotates may be relatively small. In some implementations, the inner cutting member may be a rotating tube that includes an internal lumen, and in some implementations, the inner cutting member may be a rotating rod having a larger distal blade, both with a solid cross-section.

Some implementations described herein employ an axial drive mechanism to rotate a rotational cutting member. For example, in some implementations, a pneumatic diaphragm actuator may axially displace a drive shaft in an axial or linear manner in opposite first and second directions. The drive shaft may be mechanically coupled to a drive mechanism that transforms the axial or linear motion to rotational motion, which rotates the inner cutting member. Depending on the implementation, the drive mechanism may be a cam, a swash plate, a screw drive, or other drive mechanism that may convert axial or linear motion to rotational motion. The drive mechanism may be disposed in a suitable location, including, for example and without limitation, within a graspable body or within an outer cutting tube.

The devices, systems, and methods of the present disclosure provide numerous advantages over prior cutters. For example, by providing limited rotary action, the undesired pulsatile flow associated with axial or guillotine cutters may be suitably decreased or avoided. Similarly, the undesired winding of vitreous tissue associated with continuous rotation cutters may be suitably decreased or avoided. Implementation of an efficient drive mechanism, such as a pneumatic vane actuator, may enable scalability for large and small gauge probes. For example, the drive mechanisms described herein can be implemented for a variety of gauge sizes, including 20 G, 23 G, 25 G, 27 G, and/or other suitable sizes. This may minimize the length of a rotating inner cutting member and may decrease the likelihood of spiral torsional failures. Furthermore, using a rotational blade with two cutting surfaces that permit tissue to be cut during rotation in two opposite directions may improve the cutting capacity of the probe.

FIG. 1 illustrates a vitrectomy surgical system, generally designated 100, according to an exemplary implementation. The surgical system 100 includes a base housing 102 and an associated display screen 104 showing data relating to system operation and performance during a vitrectomy surgical procedure. In some implementations, the base housing 102 may be mobile, for example, including wheels to facilitate movement as necessary. In an alternative implementation, the base housing 102 may not include wheels. The surgical system 100 includes a vitrectomy probe system 110 that includes a handheld vitrectomy probe 112, as will be discussed in more detail below with respect to subsequent figures.

Figure 2:
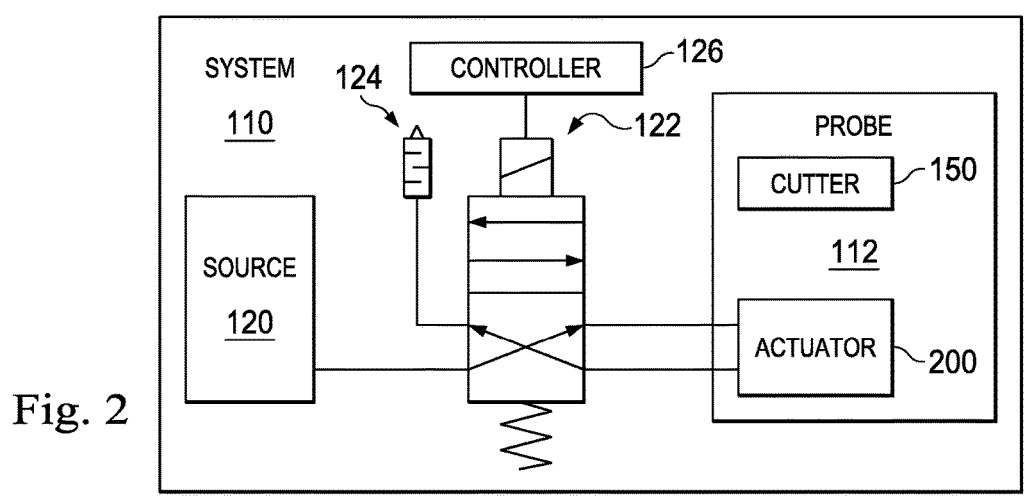
FIG. 2 is a block diagram of an example ophthalmic surgical system.

FIG. 2 is a schematic of exemplary components of the vitrectomy probe system 110. The probe system 110 includes the vitrectomy probe 112, a pneumatic pressure source 120, a probe driver (shown as an adjustable directional on-off pneumatic driver 122), a muffler 124, and a controller 126. The controller 126 may be a processor that includes one or more processing cores capable of performing parallel or sequential operations. Alternatively, the controller 126 may be a dedicated piece of hardware such as an application specific integrated circuit (ASIC), to name just a few examples. The source 120, the driver 122, the muffler 124, and the probe 112 are in fluid communication with each other along lines representing flow paths or flow lines. The controller 126 is in electrical communication with the driver 122. In some implementations, the controller 126 controls operation of both the driver 122 and various aspects of the probe 112, including the frequency of oscillation by way of the actuator 200 as well as a flow rate of fluid to and from the surgical site.

Figure 3:
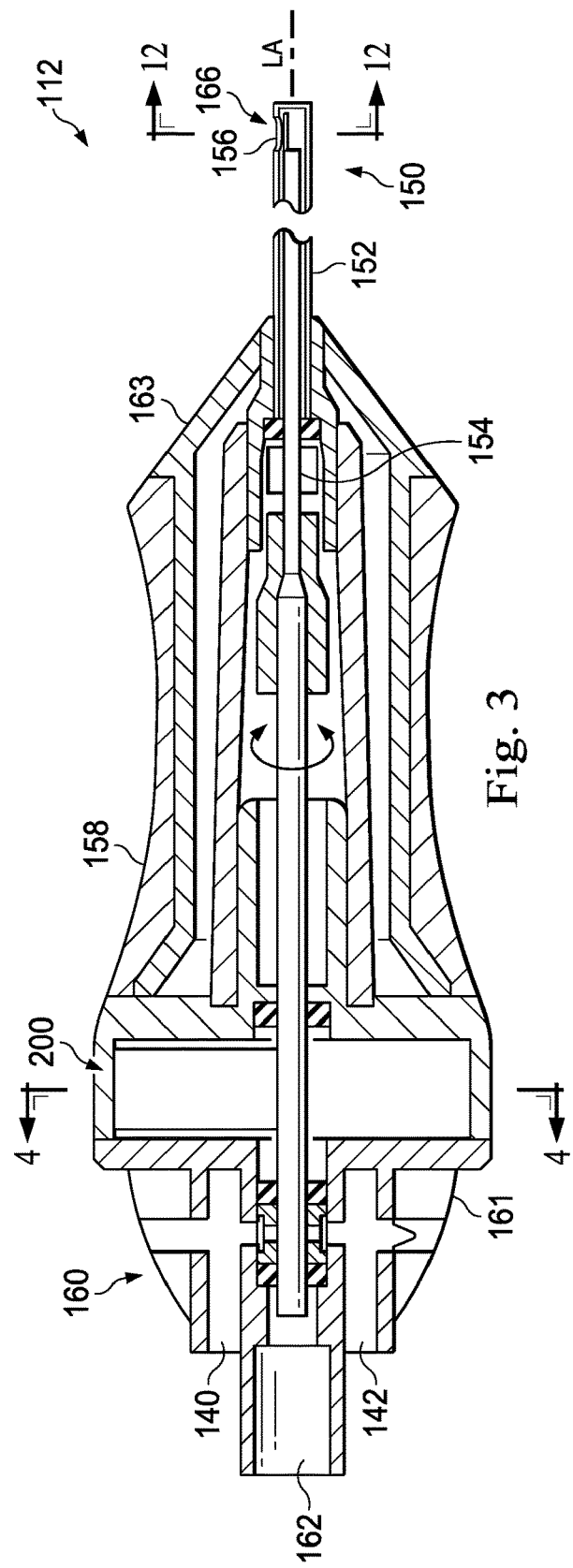
FIG. 3 is a longitudinal cross-sectional view of an example vitrectomy probe.

FIG. 3 shows a partial longitudinal cross-sectional illustration of an exemplary vitrectomy probe, for example, the vitrectomy probe 112 introduced in FIGS. 1 and 2. The vitrectomy probe 112 includes a housing 158 that is sized and shaped for grasping by a hand of a user. The probe 112 includes as its basic components a cutter 150 configured for insertion into the eye of a patient. The cutter 150 extends from a distal portion 163 of the housing 158 along a longitudinal axis LA. The cutter 150 includes an outer cutting tube 152 coupled to and extending from the housing 158. A port 156 that is sized and shaped to receive tissue within the eye is formed within the outer cutting tube 152. The cutter 150 also includes an inner cutting member 154 shown in a non-sectional side view. The inner cutting member 154 may be rotatably disposed within the outer cutting tube 152. In that regard, the inner cutting member 154 is configured to rotate about its longitudinal axis, which in this implementation, is coaxial with the longitudinal axis LA. The inner cutting member 154 is driven by a pneumatic vane actuator 200 positioned within the housing 158. In this example, the vitrectomy probe 112 is a pneumatically driven probe that operates by receiving pneumatic pressure alternating through first and second ports 140 and 142. The housing 158 includes an end piece 160 at a probe proximal end 161 with the first and second ports 140, 142 and one suction port 162 to provide aspiration of materials from the cutter 150.

Figure 4A:
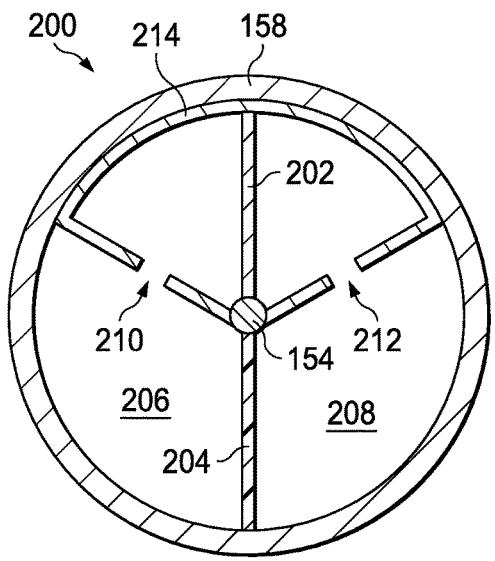
FIG. 4A is a transverse cross-sectional view of an example single vane actuator of the vitrectomy probe of FIG. 3.

FIG. 4A is a cross-sectional illustration of the exemplary pneumatic vane actuator 200 along section line 4-4 of FIG. 3. FIG. 4A illustrates a single vane actuator. The vane actuator 200 includes a vane 202 that moves in response to air pressure and/or vacuum (negative) pressure within the chambers 206, 208. In that regard, the air pressure is applied across a surface of the vane 202, which urges the vane 202 to rotate. The vane 202 is mechanically coupled to the inner cutting member 154 such that rotation of the vane 202 causes corresponding rotation of the inner cutting member 154. The chambers 206, 208 are isolated from one another by a seal 204. The vane 202 is positioned within an actuator housing 214. The actuator housing 214 includes inlets 210, 212 that direct air pressure respectively from the chambers 206, 208 to the vane 202. In that regard, the chamber 206 is in fluid communication with the first port 140 (shown in FIG. 3), and the chamber 208 is in fluid communication with the second port 142 (also shown in FIG. 3). Thus, air pressure that is received at the first port 140 is transmitted to the vane 202 via the chamber 206 and the inlet 210. Air pressure that is received at the second port 142 is transmitted to the vane 202 via the chamber 208 and the inlet 212.

Figure 5A:
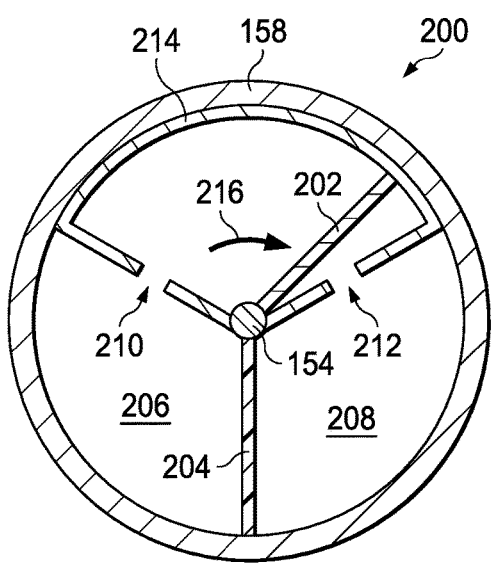
FIG. 5A is a transverse cross-sectional view of the single vane actuator of FIG. 4A with a vane in a first position.
Figure 5B:
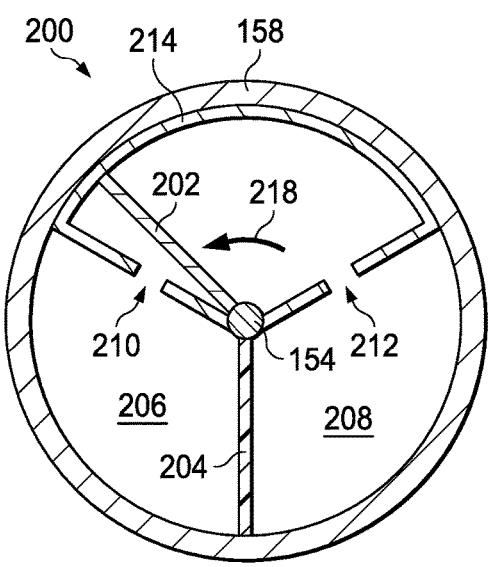
FIG. 5B is a transverse cross-sectional view of the single vane actuator of FIG. 4A with the vane in a second position.

FIGS. 5A and 5B show the vane actuator 200 in different operating positions. The operation of the vane actuator 200 is described with reference to FIG. 2, FIG. 5A, and FIG. 5B. The pneumatic driver 122 (shown in FIG. 2) may be a standard four-way on-off valve. The on-off pneumatic driver 122 may be configured to receive operating signals from the controller 126. The pneumatic driver 122 may have a solenoid or moving magnet valve that operates to move the driver to one of the two on-off positions depicted in the example of FIG. 2.

Referring to FIGS. 2 and 3, the pneumatic driver 122 is in a position to provide pneumatic pressure to the first port 140, and to vent pneumatic pressure from the second port 142. In this position, pneumatic pressure may pass from the pressure source 120, through the on-off pneumatic driver 122, and to the first port 140 where the pneumatic pressure provides pneumatic power to the vitrectomy probe 112. In particular, the pneumatic pressure acts on the vane 202 via the chamber 206 and the inlet 210 to rotate the vane in the direction 216, as illustrated in FIG. 5A. The inner cutting member 154 is correspondingly rotated in the direction 216. For example, the direction 216 may be a clockwise or counterclockwise direction. At the same time, pneumatic pressure at the second port 142 from the chamber 208 may pass through the on-off pneumatic driver 122 to the muffler 124 where it is exhausted, for example, to the atmosphere. In some instances, vacuum pressure is applied to the vane 202 via the chamber 208 and the second port 142 at the same time as pneumatic pressure is applied in the chamber 206 and the first port 140. The pneumatic pressure and vacuum pressure cooperate to rotate the vane 202 and the inner cutting member 154 in the direction 216.

In the other position, the on-off pneumatic driver 122 allows pneumatic pressure to pass from the pressure source 120 (as shown in FIG. 2) to the second port 142 (as shown in FIG. 3), where the pneumatic pressure provides pneumatic power to the vitrectomy probe 112. In particular, the pneumatic pressure acts on the vane 202 via the chamber 208 and the inlet 212 to rotate the vane in a direction 218, as illustrated in FIG. 5B. The inner cutting member 154 is correspondingly rotated in the direction 218. For example, the direction 218 may be the opposite of the direction 216. At the same time, pneumatic pressure at the first port 140 from the chamber 206 may vent through the on-off pneumatic driver 122 to the muffler 124 where it is exhausted to the atmosphere. In some instances, vacuum pressure is applied to the vane 202 via the chamber 206 and the first port 140 at the same time as pneumatic pressure is applied in the chamber 208 and the second port 142. The pneumatic pressure and vacuum pressure cooperate to rotate the vane 202 and the inner cutting member 154 in the direction 218.

Figure 6:
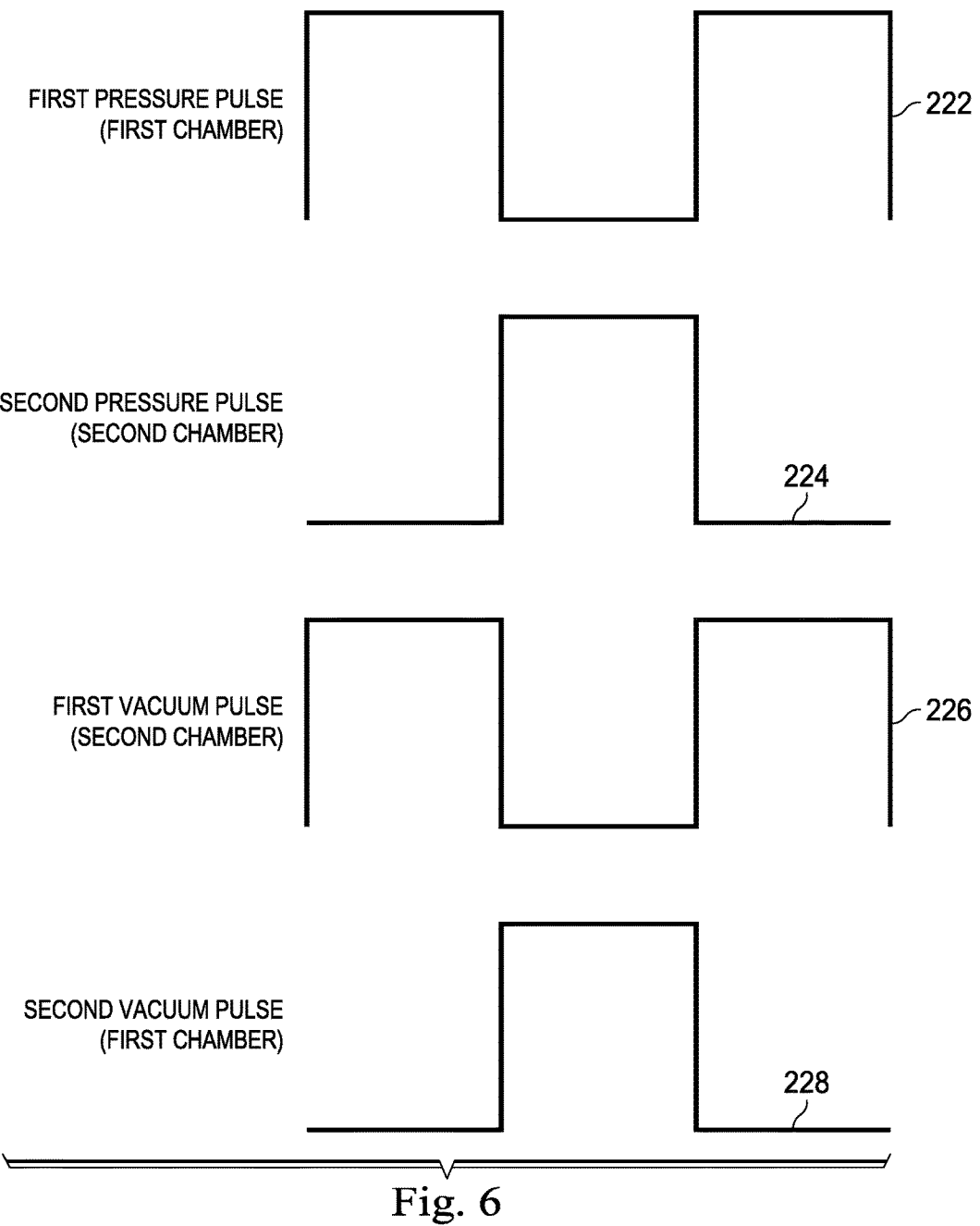
FIG. 6 is an illustration of a series of pressure pulses and vacuum pulses applied to the vane actuator of FIG. 4A.

FIG. 6 illustrates the air pressure and vacuum pressure pulses described above with respect to FIGS. 5A and 5B. The pulses 222, 224, 226, and 228 are in a high state when air pressure and/or vacuum pressure is being applied. The pulses 222, 224, 226, and 228 are in a low state when air pressure and/or vacuum pressure are not being applied. In operation, pneumatic pressure is directed alternately from the source 120 (as shown in FIG. 2) to the first and second ports 140, 142 (as shown in FIG. 3) to operate the vitrectomy probe 112. The on-off pneumatic driver 122, illustrated in FIG. 2, alternates between its two positions very rapidly to alternatingly provide pneumatic pressure to the first and second ports 140, 142. The pulses 222, 224 illustrate that the air pressure is delivered to the chamber 206 via the first port 140 and to the chamber 208 via the second port 142, respectively, in a manner that is 180° out of phase. For example, the air pressure pulse 222 is high when the air pressure pulse 224 is low and vice versa. Alternating application of air pressure to vane 202 via the chambers 206, 208 facilitates oscillation or reciprocal movement of the inner cutting member 154 with a regular frequency. The oscillation frequency of the inner cutting member 154 can correspond to the cut rate of the vitrectomy probe 112. For example, a faster oscillation frequency may correspond to a faster cut rate, and a slower oscillation frequency may correspond to a slower cut rate. In some implementations, the drive mechanisms of the present disclosure allow for a cut rate up to 10,000 cuts per minute. In other implementations, the cut rate may be up to 20,000 cuts per minute. In yet other implementations, the cut rate may be up to 30,000 cuts per minute or higher.

Vacuum or negative pressure pulses 226, 228 may also be applied in coordination with the air pressure pulses to rotate the vane 202 and the inner cutting member 154. For example, vacuum pulse 226 may be applied at the chamber 208 via the second port 142 in phase with the air pressure pulse 222 being applied at the first chamber 206 via the first port 140. For example, vacuum pulse 228 may be applied at the chamber 206 via the first port 140 in phase with the air pressure pulse 224 being applied at the second chamber 208 via the second port 142. Vacuum pulses 226, 228 are 180° out of phase from one another. While some implementations may utilize both positive air pressures (e.g., pulses 222 and 224) in combination with vacuum or negative air pressures (e.g., pulses 226 and 228), other implementations may use only positive air pressure or negative air pulses to actuate the vane 202 and the inner cutting member 154.

Figure 7A:
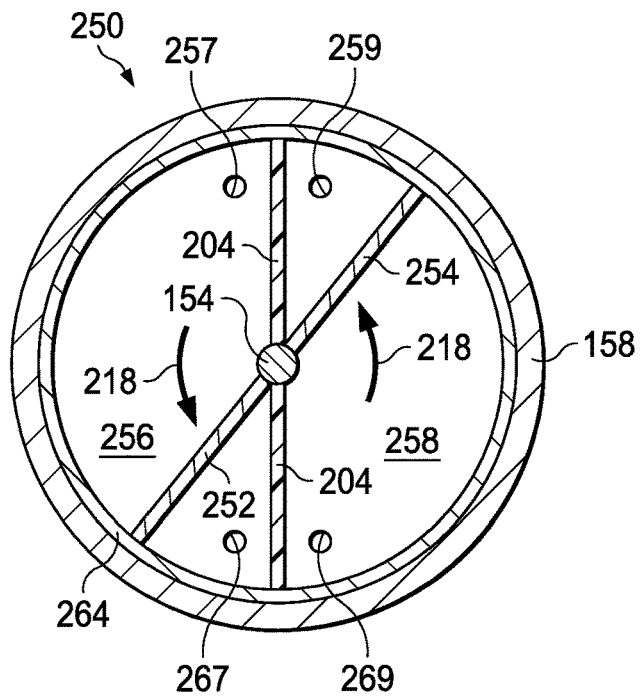
FIG. 7A is a transverse cross-sectional view of an example dual vane actuator with vanes in a first position.
Figure 7B:
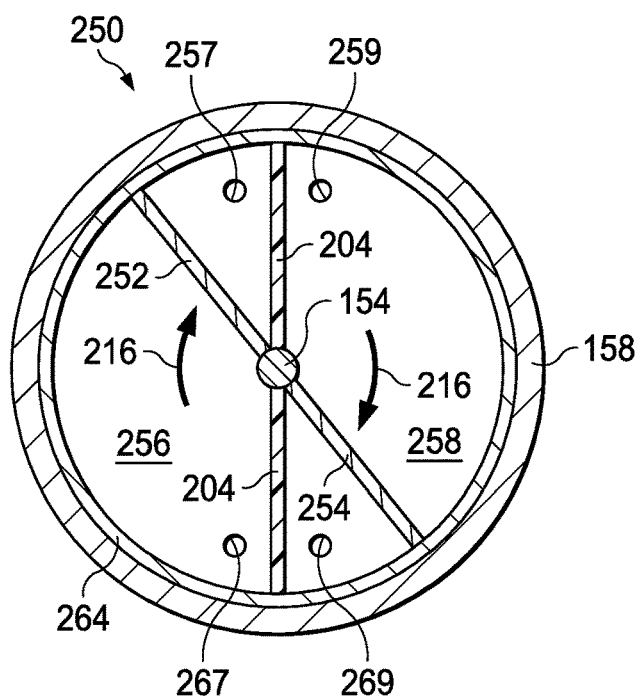
FIG. 7B is a transverse cross-sectional view of an example dual vane actuator with the vanes in a second position.

FIGS. 7A and 7B illustrate a dual vane actuator 250. In that regard, the dual vane actuator 250 can be implemented in the vitrectomy probe 112 instead of the single vane actuator 200. The vane actuator 250 includes two vanes 252, 254. Each of the vanes 252, 254 is mechanically coupled to the inner cutting member 154. Rotation of the vanes 252, 254 causes corresponding rotation of the inner cutting member 154. The implementation of two vanes 252, 254 increases (doubles) the surface area of the vanes exposed to air pressure. Accordingly, using air pressure to urge both of the vanes 252, 254 can be a more efficient way of rotating the inner cutting member 154. The vanes 252, 254 are positioned within the actuator housing 264. A seal 204 divides the actuator housing 264 into chambers 256, 258. The vane 252 is acted upon by air pressure within the chamber 256, and the vane 254 is acted upon by air pressure within the chamber 258. The chamber 256 includes inlets 257, 267 on either side of the vanes 252. The chamber 258 includes inlets 259, 269 on either side of the vane 254. The inlet 257, 259, 267, 269 may be in fluid communication with the first port 140 or the second port 142. In some implementations, the inlet 257 and the inlet 269 may be in fluid communication with the first port 140, and the inlet 259 and the inlet 267 in fluid communication with the second port 142. Other suitable combinations are contemplated. Positive or negative pressure may be selectively applied to the inlets 257, 259, 267, 269.

Referring to FIG. 7A, the pneumatic driver 122 (shown in FIG. 2) may be in a position to provide positive pneumatic pressure to the first port 140 (shown in FIG. 3). In some implementations, the pneumatic driver 122 may apply negative pneumatic pressure, e.g., a vacuum, at the second port 142 (also shown in FIG. 3). In this position, pneumatic pressure may pass from the pressure source 120, through the on-off pneumatic driver 122, and to the first port 140 where the pneumatic pressure provides pneumatic power to the vitrectomy probe 112. In particular, the positive pneumatic pressure acts on the vane 252 via the inlet 257 and the vane 254 via the inlet 269 to rotate the vanes 252, 254 in the direction 218 (as shown in FIG. 7A). From the second port 142, negative pneumatic pressure acts on the vane 252 via the inlet 267 and the vane 254 via the inlet 259 to urge the vanes 252, 254 in the direction 218. Thus, in such implementations, the pneumatic pressure and vacuum pressure cooperate to rotate the vanes 252, 254 and the inner cutting member 154 in the direction 218.

Referring to FIG. 7B, in another position of the pneumatic driver 122 (shown in FIG. 2), positive pneumatic pressure may be applied the second port 142 (shown in FIG. 3). In some implementations negative pneumatic pressure may be applied to the first port 140 (also shown in FIG. 3). In this position, pneumatic pressure may pass from the pressure source 120, through the on-off pneumatic driver 122, and to the second port 142 where the pneumatic pressure provides pneumatic power to the vitrectomy probe 112. In particular, the positive pneumatic pressure acts on the vane 252 via the inlet 267 and the vane 254 via the inlet 259 to rotate the vanes 252, 254 in the direction 216 (shown in FIG. 17B). From the second port 142, negative pneumatic pressure acts on the vane 252 via the inlet 257 and the vane 254 via the inlet 269 to urge the vanes 252, 254 in the direction 216. Thus, in some implementations, positive and negative pneumatic pressures cooperate to rotate the vanes 252, 254 and the inner cutting member 154 in the direction 216.

Figure 4B:
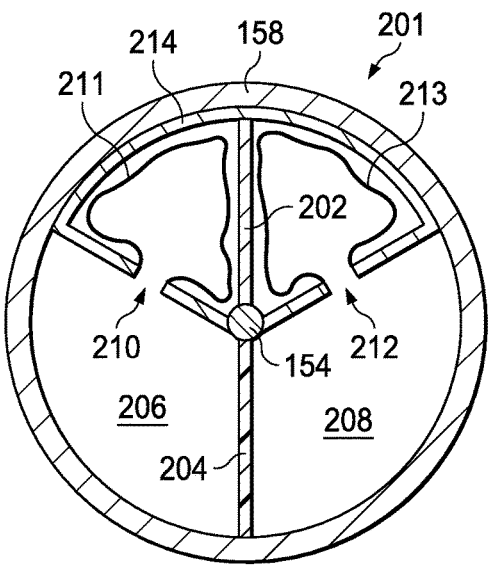
FIG. 4B is a transverse cross-sectional view of an example single vane actuator including balloons.

In some instances, the vane 202 of the vane actuator 200 and the vanes 252, 254 of the vane actuator 250 may be in contact with balloons or accordion bellows. FIG. 4B is a cross-section illustration of an exemplary pneumatic vane actuator 201, similar to the vane actuator 200 of FIG. 4A. The vane actuator 201 of FIG. 4B additionally includes balloons 211, 213. The balloon 211 is adjacently positioned on one side of the vane 202, and the balloon 213 is adjacently positioned on the other side of the vane 202. The balloon 211 is in fluid communication with the chamber 206 via the inlet 210, and the balloon 213 is in fluid communication with the chamber 208 via the inlet 212. The balloons 211, 213 serve as mediators for the air pressure acting on the vane 202. For example, in response to an air pressure pulse at the inlet 210 or the inlet 212, the balloon 211 or the balloon 213 is respectively filled and enlarged, and contacts the vane 202, urging the vane 202 to rotate. Utilizing balloons 211 and 213, instead of air pressure alone, may advantageously eliminate friction versus blow-by tolerance problems associated with vane actuators or reciprocating pistons. In some implementations, accordion bellows on either side of the vane 202 may be substituted for the balloons.

Figure 8:
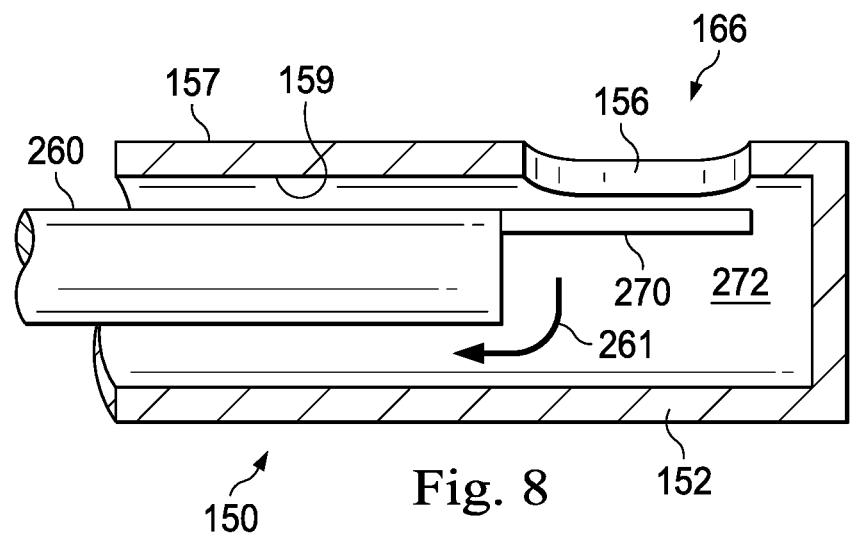
FIG. 8 is an illustration of a partial longitudinal cross-sectional view of an example distal portion of a vitrectomy probe.
Figure 9:
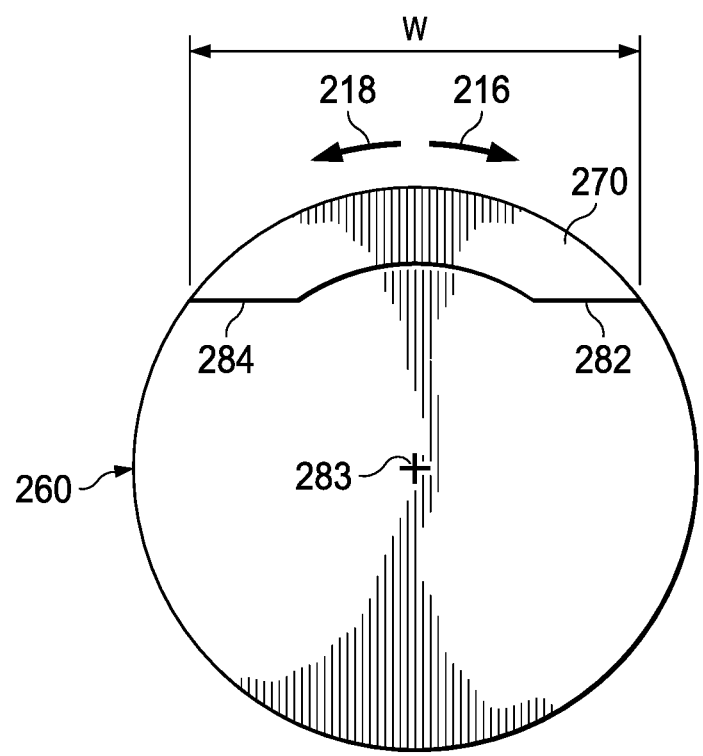
FIG. 9 is an illustration of an end view of an example inner cutting rod of a vitrectomy probe.
Figure 10:
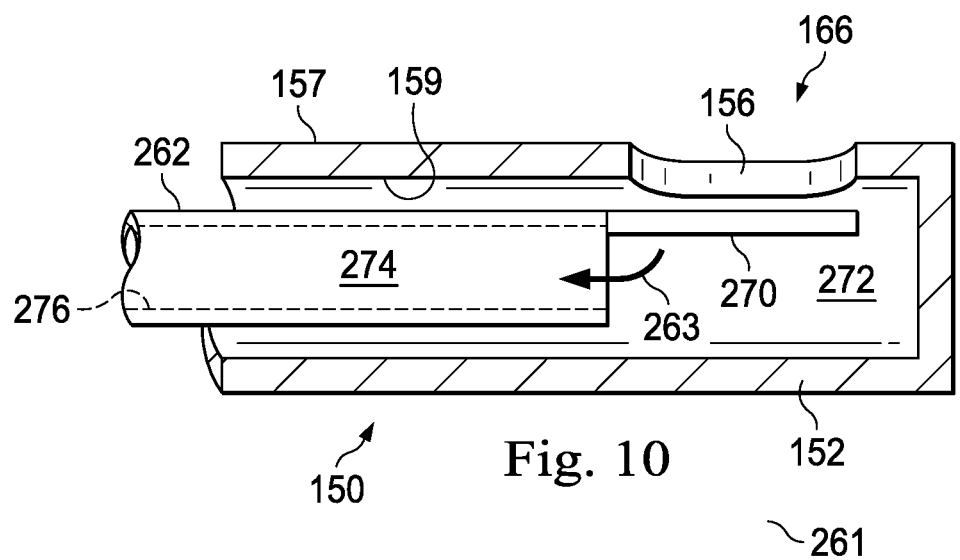
FIG. 10 is an illustration of a partial longitudinal cross-sectional view of an example distal portion of a vitrectomy probe.
Figure 11:
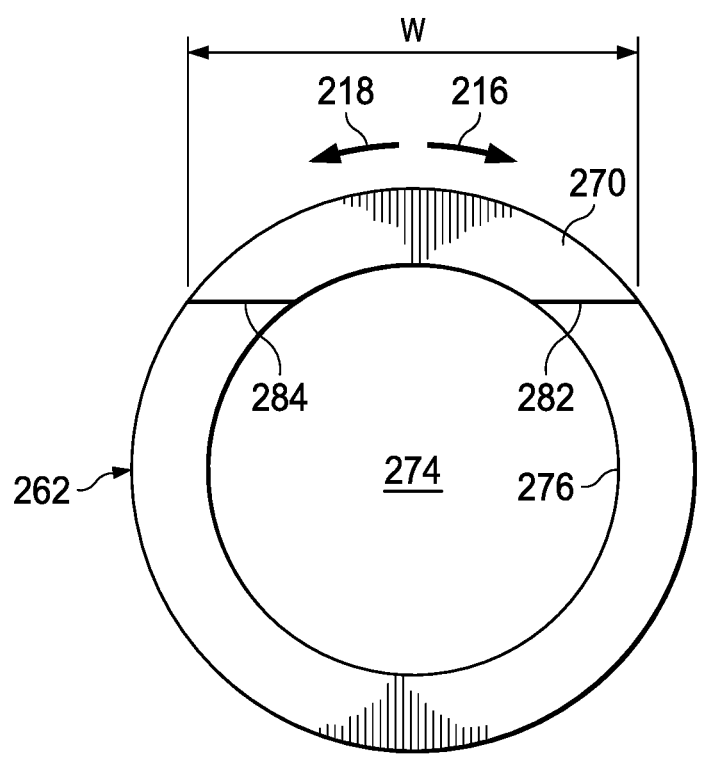
FIG. 11 is an illustration of an end view of an example inner cutting tube of a vitrectomy probe.

FIGS. 8 and 10 are partial longitudinal cross-sectional views of a distal portion 166 of the cutter 150, and FIGS. 9 and 11 are end view illustrations of inner cutting members 260, 262, respectively. The outer tube 152 has an outer surface 157 and an inner surface 159. The outer port 156 is formed within the outer tube 152 and is sized to receive tissue based on application of suction at the port 162 (shown in FIG. 2). The outer port 156 is an aperture extending from the outer surface 157 to the inner surface 159 of the outer tube 152.

In some instances, such as those illustrated in FIGS. 8 and 9, the inner cutting member 260 is a rod. In that regard, the inner cutting rod 260 may have a solid cross-section. The outer cutting tube 152 may define a lumen 272, and the inner cutting member 260 may be disposed within the lumen 272. In some instances, the inner cutting member 260 may be concentrically positioned within the lumen 272. That is, in some implementations, a central longitudinal axis of the cutting member 260 is coincident with a central, longitudinal axis of the outer cutting tube 152. In other instances, a central longitudinal axis of the inner cutting member 260 may be offset from a central longitudinal axis of the outer cutting tube 152. The inner cutting member 260 may also have an outer diameter relatively smaller than an inner diameter of the outer cutting tube 152. Tissue cut by the inner cutting member 260 may be aspirated away from the eye through a portion of the aspiration lumen 272 unoccupied by the inner cutting member 260 and in a direction indicated by the arrow 261. The lumen 272 may be in fluid communication with the suction port 162 (shown in FIG. 2) to aspirate fluid and/or cut tissue.

In other instances, such as those illustrated in FIGS. 10 and 11, the inner cutting member 262 is a tube, and defines a lumen 274 having an inner surface 276. Tissue cut by the inner cutting member 260 may be aspirated away from the eye through the aspiration lumen 274 in the direction indicated by the arrow 263. The lumen 274 may be in fluid communication with the suction port 162 (shown in FIG. 2) to aspirate fluid and/or cut tissue. The inner cutting members described herein may be implemented as a rod or a tube.

As shown in FIGS. 8 and 10 and FIGS. 9 and 11, a blade 270 is disposed at a distal-most portion of the inner cutting members 260, 262. The blade 270 may have a solid cross-section. The blade 270 has one or more cutting surfaces 282, 284. As illustrated, the cutting surfaces 282, 284 are formed along a longitudinal plane offset from a central axis 283 of the inner cutting member 260. In some implementations, one or more of the cutting surfaces 282, 284 may be formed along a plane passing through the central axis 283, thus forming a radial cutting surface. As described herein, when the blade 270 has two cutting surfaces 282, 284, the inner cutting member 260 can cut tissue in the outer port 156 during rotation in both directions 216, 218. The blade 270 may be configured to pass across the opening forming the outer port 156 to cut tissue within the outer port 156. For example, as illustrated in FIGS. 8 and 10, the blade 270 is sized to span completely across a longitudinal length of the outer port 156. The width w of the blade 270 may be based on the diameters of the outer cutting tube 152 and/or the inner cutting member 260. For example, the width w of the blade 270 may correspond to the diameter of the inner surface 159. In some implementations, the curvature of the blade 270 may match the curvature of the inner surface 159. In some implementations, the curvature of the blade 270 matches the outer diameter of the inner cutting member 260.

Figure 12A:
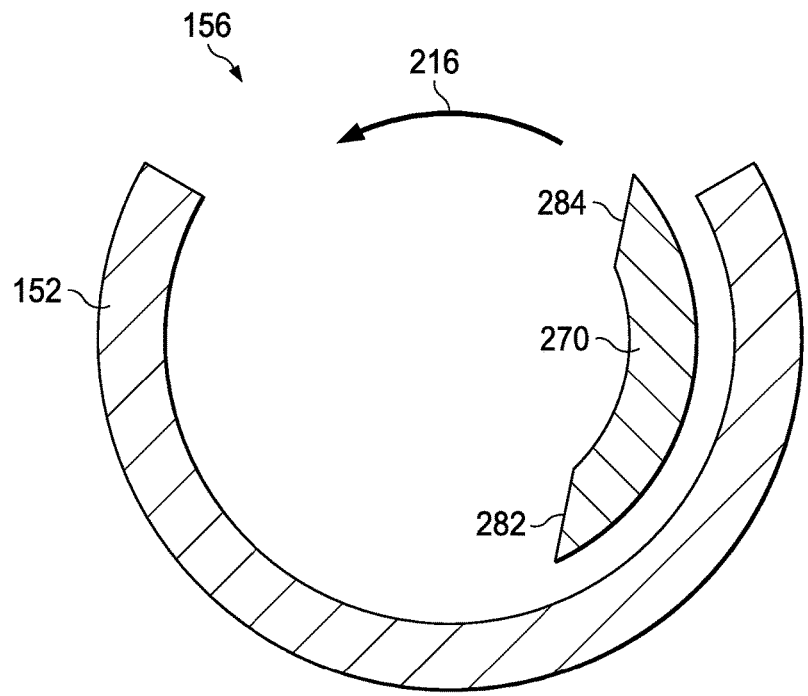
FIG. 12A is a transverse cross-sectional view of an example inner cutting member within an outer cutting tube, with the inner cutting member in a first position.
Figure 12B:
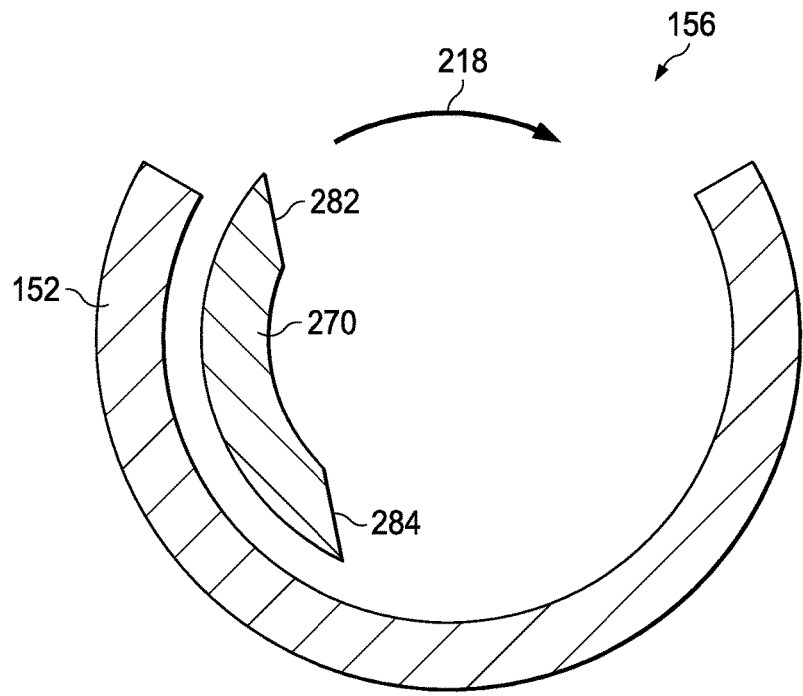
FIG. 12B is a transverse cross-sectional view of an example inner cutting member within an outer cutting tube, with the inner cutting member in a second position.

FIGS. 12A and 12B are illustrations of the blade 270 within the outer cutting tube 152 along section line 12-12 of FIG. 3. Tissue is received in the outer port 156 as result of suction at the suction port 162 (shown in FIG. 3). The blade 270 rotates between the positions illustrated in FIGS. 12A and 12B, across the outer port 156, to cut the tissue. For example, from the position of the blade 270 in FIG. 12A, the blade 270 rotates in the direction 216 across the outer port 156. During this rotation, the cutting surface 284 engages and shears the tissue at the outer port 156. The blade 270 rotates in the direction 216 in response to rotation of the one or more vanes of the vane actuator, as well as corresponding rotation of the inner cutting member, caused by application of a pressure pulse at, e.g., the port 140 (shown in FIG. 3). From the position of the blade 270 in FIG. 12B, the blade 270 may rotate in the direction 218 across the outer port 156. During this rotation, the cutting surface 282 engages and shears the tissue at the outer port 156. The blade 270 rotates in the direction 218 in response to rotation of the one or more vanes of the vane actuator, as well as corresponding rotation of the inner cutting member, caused by application of a pressure pulse at, e.g., the port 142 (as also shown in FIG. 3).

Because the blade 270 includes both cutting surfaces 282, 284, the blade 270 cuts as the blade 270 is moved in both a clockwise and a counterclockwise direction. As such, the duty cycle of the vitrectomy probe 112 may be relatively high when compared to prior systems. The duty cycle may characterize the percentage of time the blade 270 is cutting tissue relative to the total time of a complete cutting cycle of the vitrectomy probe 112. Because the blade 270 cuts while rotating in both directions 216, 218, the duty cycle is relatively higher than a blade with only one cutting surface that cuts only in one direction.

The blade 270 and the inner cutting member 260 or 262 travel in the directions 216, 218 along an arc. The arc describes a path that includes less than the 360° rotation associated with a complete revolution of the blade 270. In that regard, depending upon the implementation, the arc of the blade 270 and the inner cutting member 260 or 262 may be less than 120°. In other implementations, the arc of the blade 270 and the inner cutting member 260 or 262 may be less than 90°. In yet other implementations the arc may be less than 45°. In yet others, the arc may be less than 30°. Other arc values are also contemplated. Smaller arc values result in smaller travel distances. These in turn may enable higher reciprocation rates, resulting in higher cutting rates.

Figure 13:
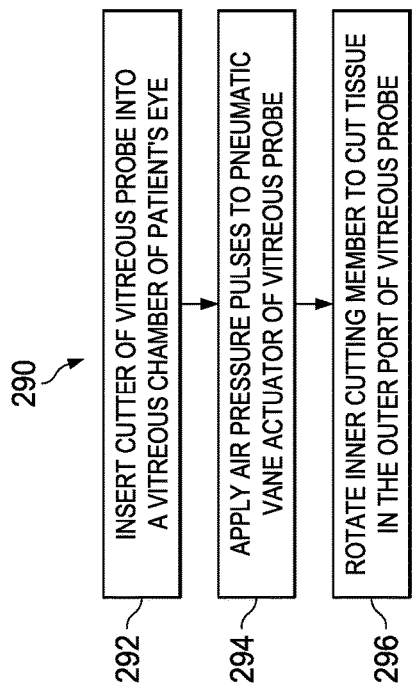
FIG. 13 is a flow diagram of an example ophthalmic surgical method.

FIG. 13 is a flow diagram of an ophthalmic surgical method 290. It is understood that the steps of method 290 may be performed in a different order than shown in FIG. 13, additional steps can be provided before, during, and after the steps, and/or some of the steps described can be replaced or eliminated in other implementations. One or more of the steps of the method 13 can be carried out by a medical professional, such as a surgeon, during an ophthalmic surgical procedure.

At step 292, the method 290 includes inserting a cutter of a vitrectomy probe, such as, for example, probe 112, into a vitreous chamber of the patient's eye. For example, a surgeon may insert at least a distal portion of the cutter, such as the distal portion 166 of the cutter 150, into the patient's eye. In that regard, the cutter can include the outer cutting tube, such as, for example, outer cutting tube 152. A distal portion of the outer cutting tube includes an outer port or aperture, such as, for example, outer port 156, that is sized and shaped to receive tissue. The cutter can also include the rotatable inner cutting member, such as, for example, inner cutting member 154, positioned within the outer cutting tube.

During a vitrectomy procedure, the surgeon typically inserts the cutter of the probe into the posterior segment and/or or vitreous chamber of the eye via an incision through the sclera in the pars plana. Such an incision is called a sclerotomy. The surgeon typically also inserts a light source and the infusion cannula into the eye via similar incisions. While viewing the posterior segment and/or vitreous chamber under a microscope and with the aid of the light source, the surgeon cuts and aspirates away vitreous using the vitrectomy probe to gain access to the area of interest (e.g., the site of a retinal detachment or tear). The surgeon may also use the vitrectomy probe to remove any membrane that has contributed to the retinal detachment. During this portion of the surgery, a saline solution is typically infused into the eye via the infusion cannula to maintain the appropriate intraocular pressure.

At step 294, the method 290 can include applying air pressure pulses to a pneumatic vane actuator of the vitrectomy probe, such as for example, vane actuator 200. For example, the air pressure pulses can be applied to the vane actuator that is disposed in the probe. The air pressure pulses act on a vane, such as, for example, vane 202, to cause rotation of the vane.

At step 296, the method 290 includes rotating the inner cutting member to cut tissue in the outer port of the vitrectomy probe. For example, the vane can be mechanically coupled to an inner cutting member, such as, for example, inner cutting member 154, such that rotation of the vane causes corresponding rotation of the inner cutting member. The distal portion of the inner cutting member may include one or more cutting surfaces, such as, for example, cutting surfaces 282, 284. Rotation of the inner cutting member causes one or more of the cutting surfaces to travel across the outer port of the outer cutting tube and cut the tissue.

In some instances, the inner cutting member is rotatable in a first direction and a second direction opposite the first direction. The vane actuator includes first and second chambers. At step 294, alternating air pressure pulses can be applied to the first and second chambers of the pneumatic vane actuator. In such instances, at step 296, the inner cutting member rotates in the first and second directions.

Figure 14A:
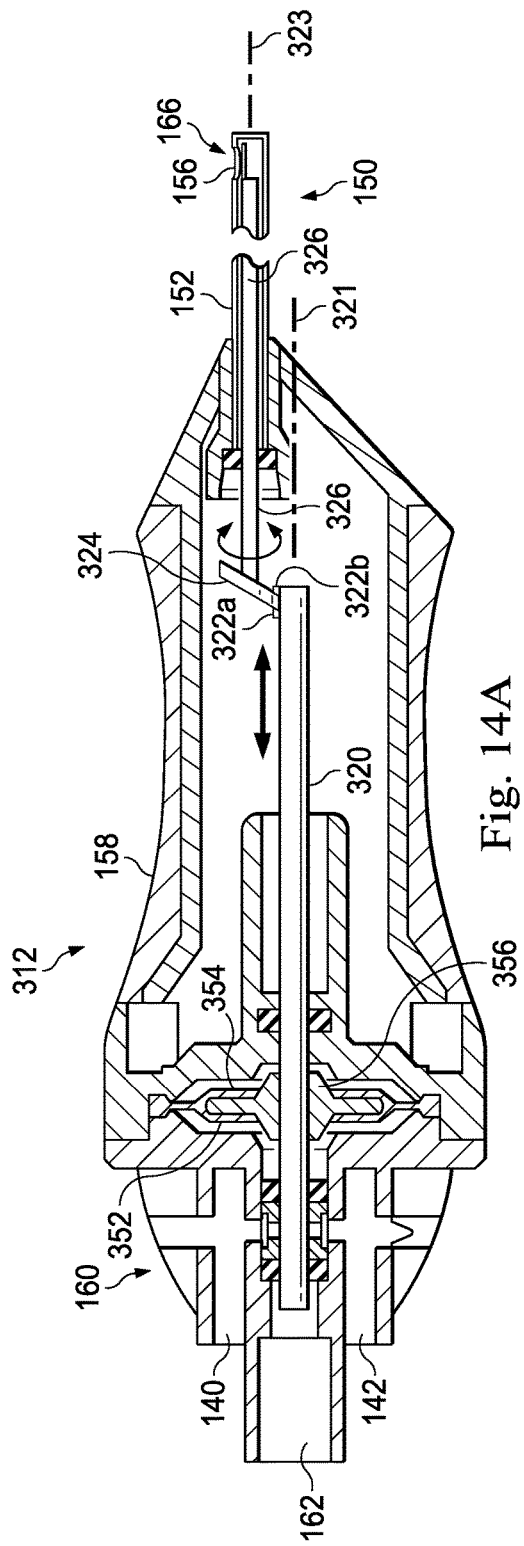
FIG. 14A is a longitudinal cross-sectional view of an example vitrectomy probe including a swash plate.
Figure 14B:
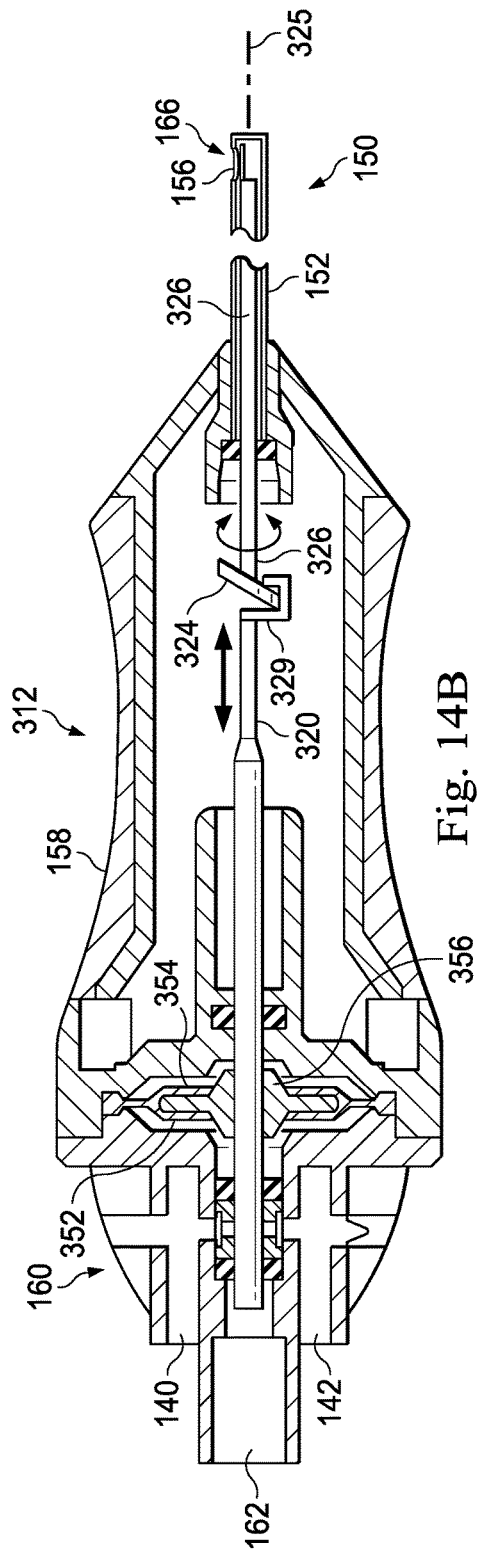
FIG. 14B is a longitudinal cross-sectional view of an example vitrectomy probe including a swash plate.

FIGS. 14A and 14B are partial cross-sectional illustrations of an exemplary vitrectomy probe 312 that converts axial displacement of a driveshaft to rotational motion in order to drive a rotational cutter. The probe 312 includes some features similar to those described with respect to the probe 112, described above, and may form a part of the vitrectomy probe system 110. The probe 312 additionally includes a drive shaft 320 positioned within the housing 158. The drive shaft 320 may be driven to reciprocate in a translational or linear manner along an axis 321 by a reciprocating air driven diaphragm 356. For example, the drive shaft 320 is driven by air pressure directed on opposing sides 352, 354 of the diaphragm 356. In that regard, the chamber 352 may be in fluid communication with the first port 140, and the chamber 354 may be in fluid communication with the second port 142. In one example of operation, if air pressure is increased at the first port 140 (and/or pressure is vented at the second port 142), the diaphragm 356 will move distally as a result of increased air pressure in the chamber 352, which displaces the drive shaft 320 in the distal direction. Venting the pressure at the first port 140 and increasing the pressure at the second port 142 moves the diaphragm 356 proximally as a result of increased air pressure in the chamber 354, which moves the drive shaft 320 in the proximal direction. Alternating air pressure pulses drive the diaphragm 356 to translate drive shaft 320 back and forth in the proximal and distal directions. In some instances, other types of actuators may be used. For example, in some implementations, a piston motor, an electric motor, and/or other types of pneumatic actuators operate in place of the diaphragm 356 to impart reciprocating translational motion to the drive shaft 320.

In this implementation, the drive shaft 320 is mechanically coupled to a drive member configured to transform the translational or linear motion of the drive shaft 320 into rotational motion of an inner cutting member 326. In FIGS. 14A and 14B, the drive member is a cam, such as a swash plate 324. In that regard, the swash plate 324 rotates about its central axis 323. The swash plate 324 is mounted at an oblique angle relative the axes 321, 323. The drive shaft 320 is mechanically coupled to the swash plate 324 by followers 322a, 322b positioned on either side of the swash plate 324. The inner cutting member 326 extends distally from the swash plate 324 along the axis 323. Because the inner cutting member 326 is mechanically coupled to the swash plate 324, rotation of the swash plate 324 causes corresponding rotation of the inner cutting member 326. In that regard, drive shaft 320 is mechanically coupled to the swash plate 324 such that reciprocal translation of the drive shaft 320 causes rotation of the swash plate 324 and corresponding rotation of inner cutting member 326. Inner cutting member 326 may rotate along an arc in opposite first and second directions to cut tissue in the outer port 156, as described herein. In other instances, other suitable drive members, such as a screw drive, may be implemented to convert translational or linear motion of the drive shaft 320 into rotational motion at the inner cutting member 326.

In the implementation of FIG. 14A, the axis 321 of the drive shaft 320 and the axis 323 of the inner cutting member 326 are offset from one another. FIG. 14B illustrates an implementation in which the drive shaft 320 and the inner cutting member 326 are aligned. In that regard, the drive shaft 320 can be mechanically coupled to the swash plate 324 via a U-shaped distal portion 329. Translation of the drive shaft 320 along the axis 325 causes rotation of the swash plate 324 and corresponding rotation of the inner cutting member 326 about the axis 325.

Figure 15:
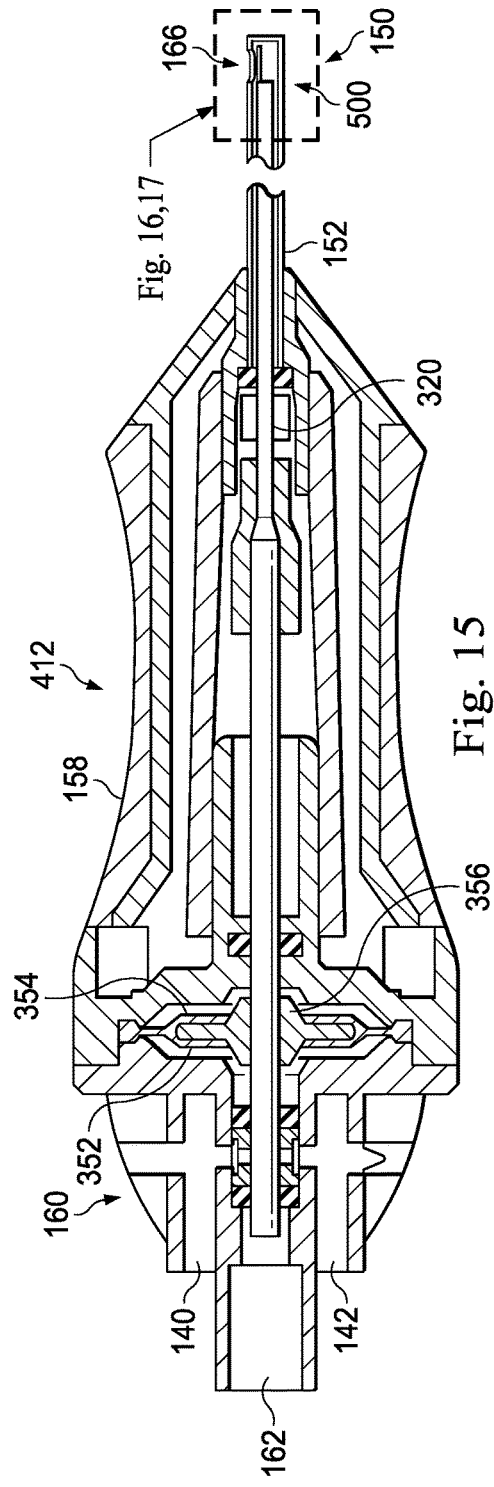
FIG. 15 is a longitudinal cross-sectional view of an example vitrectomy probe.
Figure 16:
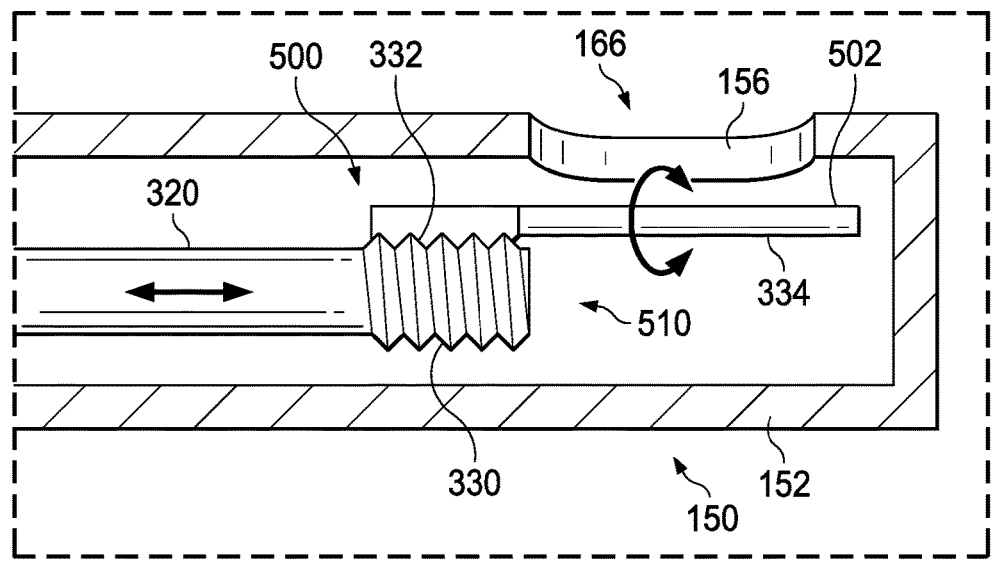
FIG. 16 is a partial longitudinal cross-sectional view of an exemplary distal portion of the vitrectomy probe of FIG. 15.
Figure 17:
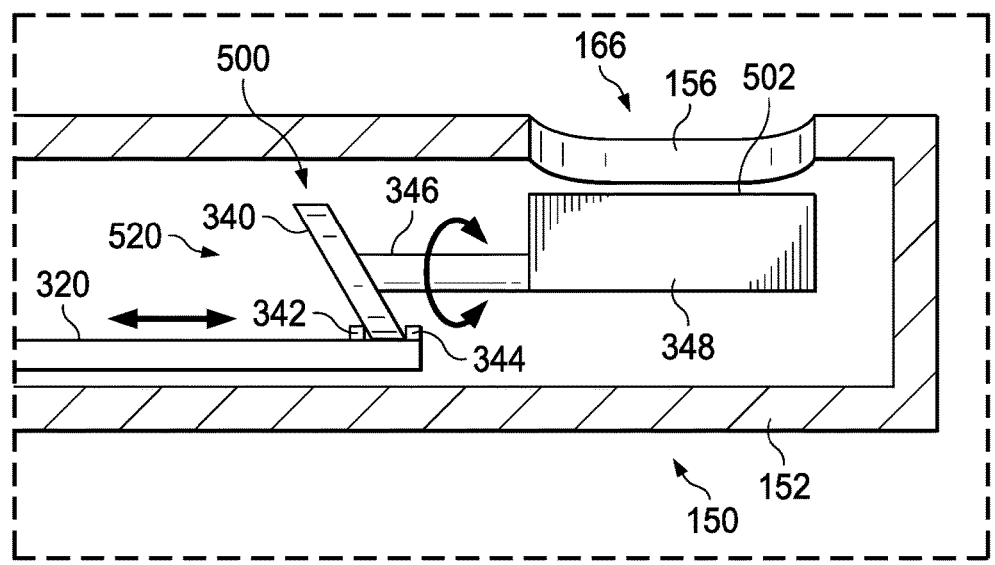
FIG. 17 is a partial longitudinal cross-sectional view of an exemplary distal portion of the vitrectomy probe of FIG. 15.

FIG. 15 is a partial cross-sectional illustration of an exemplary vitrectomy probe 412. The probe 412 includes some features similar those described with respect to the probe 112 and the probe 312, described above. Implementations of the distal portion 166 of the probe 412 are illustrated in FIGS. 16 and 17. As shown, a drive member 500 is configured to transform the translational or linear motion of the drive shaft 320 into rotation motion of the inner cutting member 502 as positioned within the outer cutting tube 152. The drive member 500 in FIG. 16 is screw drive 510, and the drive member 500 in FIG. 17 is swash plate 520. Other suitable drive members configured to transform translational or linear motion into rotational motion are also contemplated. Implementing the drive member within the outer cutting tube 152, and particularly at a distal portion of the outer cutting tube 152, advantageously reduces the length of the inner cutting member 334, as shown in FIG. 16, and 346, as shown in FIG. 17. Because only the inner cutting member of a relatively shorter length rotates at a high rate, the likelihood of spiral torsional failures is reduced. The inner cutting member can also be implemented as a rod in some instances.

FIG. 16 illustrates a screw drive 510 implemented within the outer cutting tube 152. A distal portion of the drive shaft 320 includes screw threads 330 that engage the corresponding threads 332 of the inner cutting member 334. The screw threads 330, 332 engage in a manner that converts the translational linear motion of the drive shaft 320 into rotational motion of the inner cutting member 334. The inner cutting member 334 may rotate along an arc in opposite first and second directions to cut tissue in the outer port 156, as described herein.

FIG. 17 illustrates a swash plate 340 implemented within the outer cutting tube 152. The drive shaft 320 is mechanically coupled to the swash plate 340 via followers 342, 344 positioned on either side of the swash plate 340. The inner cutting member 346 extends distally from the swash plate 340. A distal portion of the inner cutting member 346 includes a blade 348 having one or two cutting surfaces, as described herein. Because the inner cutting member 346 is mechanically coupled to the swash plate 340, rotation of the swash plate 340 causes corresponding rotation of the inner cutting member 346. In that regard, drive shaft 320 is mechanically coupled to the swash plate 340 such that reciprocal translation of the drive shaft 320 causes rotation of the swash plate 340 and corresponding rotation of inner cutting member 346. Inner cutting member 346 and the blade 348 may rotate along an arc in opposite first and second directions to cut tissue in the outer port 156, as described herein.

Figure 18:
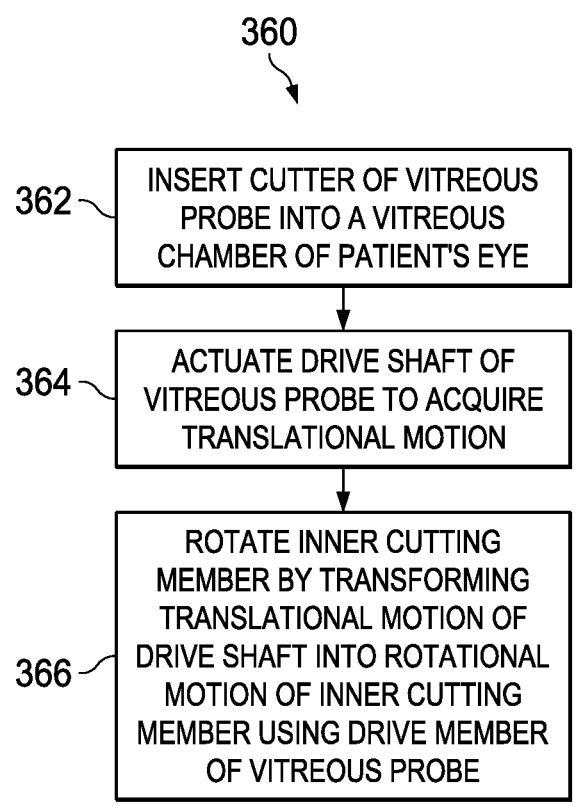
FIG. 18 is a flow diagram of an example ophthalmic surgical method.

FIG. 18 is a flow diagram of an ophthalmic surgical method 360. It is understood that the steps of method 360 may be performed in a different order than shown in FIG. 18, additional steps can be provided before, during, and after the steps, and/or some of the steps described can be replaced or eliminated in other implementations. One or more of steps of the method 360 can be carried out by a medical professional, such as a surgeon, during an ophthalmic surgical procedure.

At step 362, the method 360 includes inserting a cutter of a vitrectomy probe into a vitreous chamber of the patient's eye. For example, a surgeon may insert at least a distal portion of a cutter 150, such as, for example, distal portion 166 of cutter 150 as shown in FIGS. 14A-17, into the patient's eye. The cutter includes the outer cutting tube, such as, for example, outer cutting tube 152. A distal portion of the outer cutting tube includes an outer port or aperture, such as, for example, outer port 156, that is sized and shaped to receive tissue. The cutter can also include a rotatable inner cutting member positioned within the outer cutting tube. The step 362 may be similar to the step 292, shown in FIG. 13.

At step 364, the method 360 includes actuating a drive shaft of the vitrectomy probe, such as, for example, drive shaft 320, such that the drive shaft acquires translational or linear motion. For example, the drive shaft can be actuated by a pneumatic diaphragm actuator, e.g., pneumatic diaphragm actuator 356, and/or other suitable actuator. The drive shaft can be reciprocally translated in response to alternating air pressure pulses applied at the ports, e.g., ports 140, 142, to cause the actuator to move the drive shaft.

At step 364, the method 360 includes rotating the inner cutting member. For example, the translation or linear motion of the drive shaft can be transformed into rotational motion of the inner cutting member using a drive mechanism of the vitrectomy probe. The drive mechanism can be a cam, such as a swash plate, and/or a screw drive. In some instances, the drive mechanism can be positioned within the outer cutting tube.

Implementing the systems, methods, and devices disclosed herein may provide advantages not obtained by conventional by vitrectomy probes. The advantages described herein may provide smoother fluid flow while having only minimal risk of undesirably winding vitreous tissue. Furthermore, a drive member disposed at a distal end of the vitrectomy probe may minimize the length of a rotating inner cutting member and may decrease the likelihood of spiral torsional failures. Furthermore, using a rotational blade with two cutting surfaces that permit tissue to be cut during rotation in two opposite directions may improve the cutting capacity of the probe.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic surgical system, the system comprising: a vitrectomy probe comprising: a housing sized and shaped for grasping by a user; a cutter sized to penetrate an eye, the cutter extending from the housing, wherein the cutter comprises: an outer cutting tube coupled to the housing, the outer cutting tube having an outer port formed therein, wherein the outer port is sized and shaped to receive tissue; and an inner cutting member disposed within the outer cutting tube, the inner cutting member rotatable about a longitudinal axis thereof, the inner cutting member comprising a first cutting surface that rotates across the outer port to cut the tissue when the inner cutting member is rotated; a drive shaft disposed within the housing; an actuator coupled to the drive shaft and disposed within the housing, the drive shaft linearly reciprocable in response to actuation by the actuator; and a drive member coupled to the drive shaft and the inner cutting member, the inner cutting member rotatable about the longitudinal axis thereof in response to the linear reciprocable motion of the drive shaft, wherein the drive member comprises a swash plate.

2. The system of claim 1, wherein the drive member is disposed in the outer cutting tube.

* * * * *